United States Patent [19]

Meilland

[11] Patent Number: Plant 7,541

[45] Date of Patent: Jun. 4, 1991

[54] ROSE PLANT — MEILVAR VARIETY

[75] Inventor: Alain A. Meilland, Antibes, France

[73] Assignee: The Conard-Pyle Company, West Grove, Pa.

[21] Appl. No.: 482,716

[22] Filed: Feb. 21, 1990

[51] Int. Cl.[5] ..... A01H 5/00
[52] U.S. Cl. ..... Plt./15
[58] Field of Search ..... Plt./15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive fragrant very double aureolin blossoms. Such blossoms are long lasting and their coloration tends to be stable. The plant exhibits an erect growth habit, very vigorous vegetation, and is well suited for use as a decorative planting in parks and gardens. Additionally, the plant exhibits excellent disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meidragelac variety (nonpatented in the United States). The male parent (i.e., the pollen parent) was the Meikinosi variety (nonpatented in the United States). The Meikinosi variety sometimes is known as the Tchin-Tchin variety. The parentage of the new variety can be summarized as follows:

Meidragelac × Meikinosi.

The seeds resulting from the above pollination were sown and 184 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive fragrant long lasting very double aureolin blossoms of good color stability,
(b) exhibits an erect growth habit,
(c) exhibits very vigorous semi-dull vegetation,
(d) is particularly suited for growing in parks and gardens, and
(e) exhibits good disease resistance.

The rose plant is well-balanced, very clean in appearance and possesses decorative foliage in combination with the attractive blossoms.

The new variety well meets the needs of the horticultural industry for all uses and is particularly well suited for use as a decorative planting in parks and gardens.

The new variety has been found to undergo asexual propagation by a number of routes, including budding, grafting, cuttage, etc. The characteristics of the new variety have been found to be stable and are strictly transmissible by such asexual propagation from one generation to another.

The new variety has been named the Meilivar variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelli* understock and growing outdoors at LeCannet des Maures, Var, France.

DETAILED DESCRIPTION

Figures 1, 2, 3, 4, 5, 6, 7, 8, 9, 10, 11, 12, 13, 14, 15, 16:
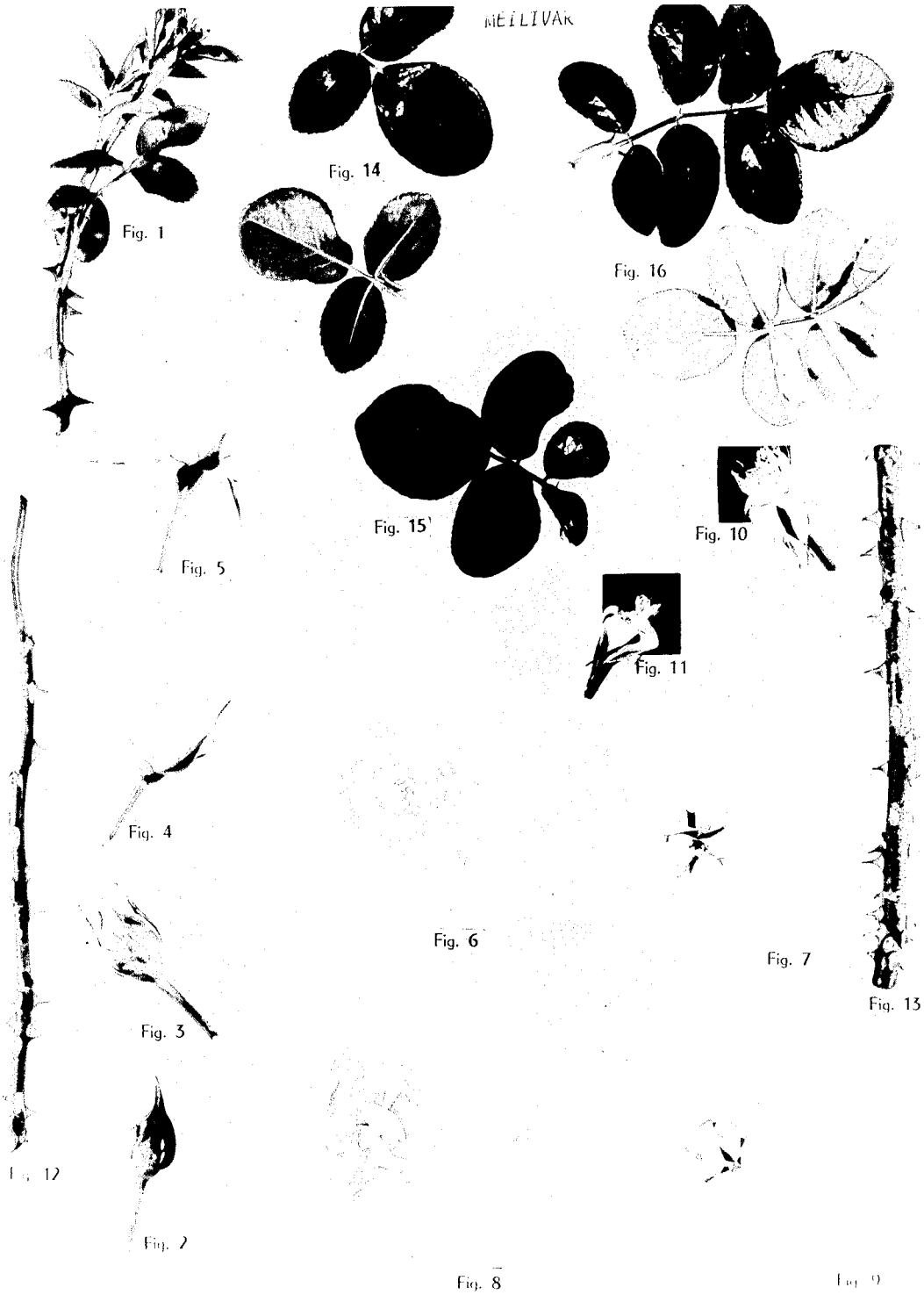
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of two leaves with three leaflets — plan view — with the upper surface being shown on the top and the under surface being shown on the bottom.
FIG. 15 illustrates specimen of a leaf with five leaflets — plan view — upper surface.
FIG. 16 illustrates specimens of two leaves with seven leaflets — plan view — with the upper surface being shown on the top and the under surface being shown on the bottom.

The chart used in the identification of the colors is that of The Royal Horticultural Society (R.H.S. Colour Chart). The description is based on the observation of two year old plants made during September while budded on *Rosa froebelli* understock and growing outdoors at LeCannet des Maures, Var, France. The coloration in common terms precedes reference to the chart.

Class: Hybrid tea.

Plant:

*Height.*—Approximately 90 to 100 cm. on average.

*Habit.*—Upright.

Branches:

*Color.*—Young stems: lettuce green, Yellow-Green Group 144A. Adult wood: medium green, Yellow-Green Group 146B.

*Thorns.*—Size: large. Quantity: average. Color: reddish on young stems and pinkish changing to tan on adult wood.

Leaves:

Stipules.—Adnate, pectinate, somewhat wide, and green in coloration.

*Petioles.*—Upper surface: striped reddish brown on young foliage and medium green on mature foliage with more or less glandular edges. Under surface: light green, bear a few prickles.

Leaflets.—Number: 3, 5, and 7 (most often). Shape: oval. Serration: single and regular. Texture: leathery. General appearance: semi-dull and dense foliage. Color (young foliage): upper surface: bronze green, Yellow-Green Group 146A. under surface: light green, Yellow-Green Group 147C. Color (adult foliage): upper surface: bronze green, Yellow-Green Group 146A. under surface: light green, Yellow-Green Group 147C.

Inflorescence:

*Number of flowers.*—Generally one per stem.

*Peduncle.*—Straight, rigid, light green in coloration. The length is approximately 3 to 4 cm. on average.

*Sepals.*—Upper surface: tomentose, greenish in coloration. Under surface: light green and more or less tinted with reddish coloration, the edges are glandular and only slightly appendiculated.

*Buds.*—Shape: oval. Length: approximately 4 cm. on average. Size: large. Color upon opening: upper surface: Yellow Group 7A. under surface: aureolin, Yellow Group 12B.

*Flower.*—Shape: as a hollow cup and very double. Diameter: approximately 12 to 13 cm. on average. Color (when opening begins): upper surface: Yellow Group 7A. under surface: aureolin, Yellow Group 12B. Color (when blooming): upper surface: aureolin, Yellow Group 12A. under surface: aureolin, Yellow Group 12B. Color (at end of opening): upper surface: barium yellow, Yellow Group 10B. under surface: barium yellow, Yellow Group 10B. Fragrance: fairly strong. Lasting quality: long. Petal number: approximately 98 to 114 on average. Texture: consistent. Petal drop: good. Stamen number: approximately 103 to 110 on average. Anthers: normal and bright yellow in coloration. Filaments: bright yellow in coloration, of irregular heights. Pistils: approximately 85 to 93 on average. Stigmas: normal, ochre in coloration.

Styles: greenish at base and light fuschia at top, of irregular heights. Receptacle: smooth, medium green, in longitudinal section it is wide and in the shape of a funnel.

Development:

*Vegetation.*—Vigorous.

*Blooming.*—Very abundant and continuous throughout the season.

*Aptitude to bear fruits.*—Poor.

*Resistance to frost.*—Good.

*Resistance to diseases.*—Very good.

I claim:

1. A new and distinct variety of Hybrid Tea Rose plant characterized by the following combination of characteristics:

(a) forms in abundance on a continuous basis attractive fragrant long lasting very double aureolin blossoms of good color stability.

(b) exhibits an erect growth habit, (c) exhibits very vigorous semi-dull vegetation, (d) is particularly suited for growing in parks and gardens, and (e) exhibits good disease resistance;

substantially as herein shown and described.

* * * * *

MEILIVAK